United States Patent
Mooney et al.

(10) Patent No.: US 6,231,872 B1
(45) Date of Patent: *May 15, 2001

(54) STRUCTURED OCCLUSIVE DRESSINGS

(75) Inventors: Mark Mooney, Somerset; Anthony Gallo, Warren, both of NJ (US); John Perucki, Washington Crossing, PA (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/153,408

(22) Filed: Sep. 15, 1998

Related U.S. Application Data

(63) Continuation of application No. 08/560,248, filed on Nov. 21, 1995, now Pat. No. 5,814,031, which is a continuation-in-part of application No. 08/397,596, filed on Mar. 2, 1995, now abandoned.

(51) Int. Cl.$^7$ .............................. A61L 15/16; A61K 9/14
(52) U.S. Cl. ........................ 424/400; 424/443; 424/445; 424/446; 424/447; 424/448; 424/449; 424/485; 424/486; 424/487
(58) Field of Search ................................ 424/400, 443, 424/445–9; 485/487

(56) References Cited

U.S. PATENT DOCUMENTS

| | | | |
|---|---|---|---|
| 5,429,592 | * | 7/1995 | Jensen ..................................... 602/59 |
| 5,512,041 | * | 4/1996 | Bogart .................................... 602/58 |
| 5,814,031 | * | 9/1998 | Mooney et al. ...................... 604/307 |

\* cited by examiner

*Primary Examiner*—S. Mark Clardy
*Assistant Examiner*—Katryne E. Shelborne
(74) *Attorney, Agent, or Firm*—Lawrence D. Schuler; Frederick L. Herman

(57) ABSTRACT

This invention relates to a composition containing a hydrophobic solvent, a network polymer and a flow control agent which is useful in healing wounds. The composition of this invention may be applied directly to a wound to create a structured occlusive dressing. The dressings of this invention do not migrate, but maintain their integrity at skin temperature, and encourage the creation of a moist wound environment while protecting the wound in order to accelerate healing.

58 Claims, 12 Drawing Sheets

STRUCTURED OCCLUSIVE DRESSINGS

CROSS REFERENCE TO RELATED APPLICATION

This is a continuation of U.S. patent application Ser. No. 08/560,248 filed Nov. 21, 1995, now U.S. Pat. No. 5,814,031 which is a continuation-in-part of U.S. patent application Ser. No. 08/397,596, filed Mar. 2, 1995 by Schiraldi et al. (hereinafter "the Schiraldi application"), now abandoned, the disclosure of which is hereby incorporated by reference.

FIELD OF THE INVENTION

This invention relates to a structured wound dressing which remains in place and does not flow, but has an ointment-like feel. The invention also relates to adhesive bandages comprising the aforementioned structured dressing.

BACKGROUND OF THE INVENTION

For many years, people have cared for wounds or other skin insults using absorbent bandages as coverings. It is well-documented ("Epidermal Wound Healing", H. I. Maibach, D. T. Rovee, editors, YearBook Medical Publishers, Inc., 1972) that wounds heal faster when covered and kept moist while being protected from additional abrasion and exposure.

In order to protect the wound further from becoming infected, some individuals apply antiseptic or antibiotic agents to the wound prior to bandaging. These medicinal agents may be applied in the form of a liquid, or a water-in-oil emulsion such as an ointment or cream. However, these formulations tend to run, in the case of liquids, or ooze out from under the bandage. Thus, maintaining the position of the medicinal agent in close proximity to the wound in order to impart medicinal activity to the wound is quite difficult. It would be desirable for such consumers to be able to apply a medicament which will not migrate from the wound, i.e., a "structured" dressing.

This object, however, is quite difficult to achieve. For example, many of the ointments used in antiseptic and antibiotic formulations are petrolatum-based. However, by their nature, ointments, particularly ointments based on petrolatum, flow fairly easily. Consumers feel comfortable using such petrolatum-based products and are accustomed to the sensation of wearing the ointment in conjunction with adhesive bandages. Thus, any attempt at creating a stable, "structured" base for medicinal application should have an ointment "feel".

Many individuals apply adhesive bandages to their smaller cuts and abrasions. similarly, they apply gauze or other types of coverings to larger skin wounds. It would be highly desirable for such wound-coverings to have, incorporated within their structures, medicinal agents to combat wound infection. This would afford consumers a great convenience. Conventional ointments and petrolatum-based formulations tend to be too runny and messy for incorporation with a wound-covering material.

Therefore, it is an object of this invention to provide a structured material which can serve as a base for maintaining a covering over a wound.

It is another object of this invention to provide a structured material which can serve as a base for maintaining an occlusive covering over a wound.

It is another object of this invention to provide a wound dressing having an antibiotic or antiseptic agent incorporated in its structure.

Yet another object of this invention is to provide a structured material which can serve as a base for applying medicaments to a wound.

Still another object of this invention is to provide a pressure sensitive adhesive coated material which can serve as a base for maintaining in place the structured wound dressing.

A further object of this invention is to provide a structured material for use in a wound-dressing that has an ointment-like feel but which retains its position over a wound without flowing.

Yet another object of this invention is to provide a structured material for use in a wound-dressing that adheres to intact skin yet easily releases from an open wound without retraumatizing the wound.

Additional objects will become evident in the ensuing description of the invention.

SUMMARY OF THE INVENTION

This invention relates to a composition containing a hydrophobic solvent base and a combination of polymers which create a structured occlusive dressing having a high viscosity and an ointment-like feel.

More particularly, this invention relates to a composition containing a hydrophobic solvent base, a network polymer and a flow control polymer which results in a high-viscosity, structured dressing. Due to its high viscosity and its hydrophobicity, the structured dressing of this invention is believed to provide unique drug delivery characteristics. It permits the addition of drugs to the dressing which may otherwise be irritation-producing but, in the dressing of this invention, do not irritate the skin.

The structured occlusive dressings of this invention may be applied directly to the skin, or they may be incorporated into a combination dressing and be attached directly to a substrate such as a covering material or bandage. The covering material may be a woven or nonwoven fabric or a film material, or a combination thereof.

DETAILED DESCRIPTION OF THE PREFERRED EMBODIMENTS

Figure 1:
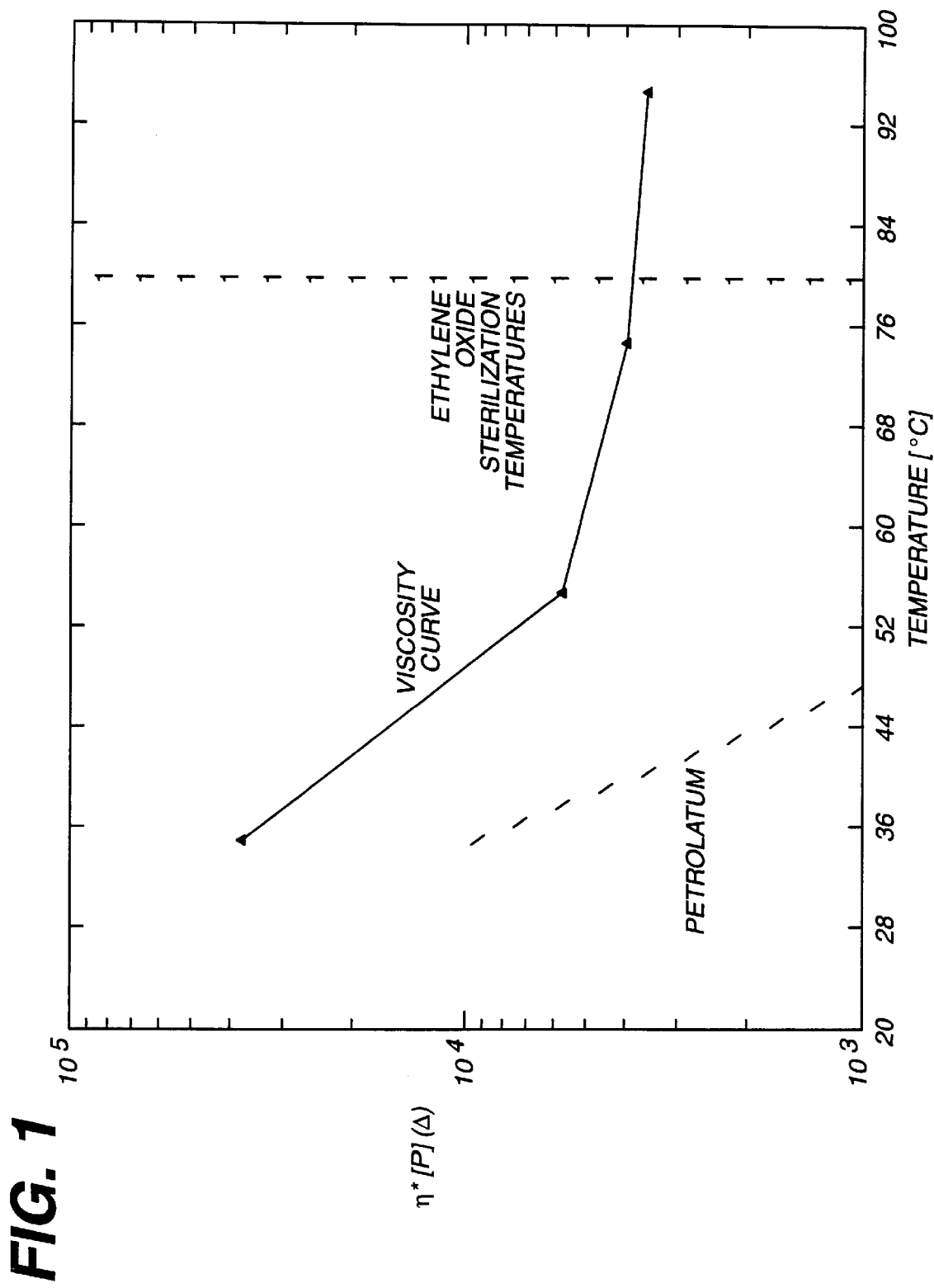
FIG. 1 is a plot showing viscosity as a function of temperature for petrolatum and for one of the occlusive compositions of the present invention.

The compositions of this invention generally contain a hydrophobic solvent or a combination of hydrophobic solvents and other additives resulting in a structured dressing that does not readily flow. The structured dressings of this invention may be an oil-phase composition or a water-in-oil emulsion.

The hydrophobic solvent may be a hydrocarbon material, such as petrolatum, mineral oil or the like. It may also be composed of fatty acids such as castor oil or similar material. Alternatively, the hydrophobic solvent constituent may contain a wax in addition to other solvents, such as paraffin wax, microcrystalline wax, beeswax or the like. This element of the composition serves as the "oil base" of the solvent or the emulsion and makes up a large proportion of the composition, up to 90%. This solvent imparts the ointment "feel" to the composition. The solvent also provides occlusion, contributes to the regulation of drug delivery and is the primary means by which the dressings of this invention achieve superior wound release characteristics. Preferably, it is a fluid, semi-solid or solid at room or skin temperature (from about 55° F. to about 100° F.) having a viscosity of from about 1 to about 100,000 centipoise. Thus, any hydrocarbon material or combination of materials which have the appropriate viscosity at the desired temperatures may be used in the products of this invention.

A combination of members of two classes of polymers and/or additives should be added to the hydrophobic solvent to make the compositions of this invention. The first class of polymers can be generally termed "network" polymers. These polymers increase the viscosity of the solvent or emulsion and provide gel strength to the solvent or emulsion. The second class of polymers can be generally termed "flow control" polymers, which assist in controlling the flow characteristics of the dressings of this invention.

Gel strength can be measured by the relationship between the viscosity of the composition and temperature. Network polymers show a "plateau" in this type of measurement, i.e., the viscosity of the composition displays little or no change over a wide temperature range. The value of the viscosity at this plateau is defined as the gel strength. Preferably, in the compositions of this invention, the gel strength should be from about 1000 to about 10,000 poise over a temperature range of from about 50° C. to 95° C.

Gel strength is particularly important in manufacturing and processing sterile bandages and wound dressings. The products are often subjected to ethylene oxide sterilization processes at high temperatures (about 175 –180° F., 80–82° C.). The products of this invention should be able to withstand such temperatures without causing the structured ointments of this invention to flow readily into the primary packaging or into the pressure sensitive adhesive. Such ready flow would compromise sterility or affect the ability of adhesive to adhere to skin.

Preferably, the polymers that are useful in the compositions of this invention to create gel strength are block copolymers. Di-, tri- and multiarm block copolymers of polystyrene and synthetic rubber where the rubber is preferably isoprene, ethylene butadiene, ethylene propylene or the like or combinations thereof are useful as network polymers in the dressings of this invention. Examples of such polymers are KRATON di- and tri-block copolymers commercially available from the Shell Chemical Company and the like. The KRATON polymers are described by the Shell Chemical Company as elastomers which have a combination of high strength and low viscosity. These polymers contain block segments of styrene monomer units and rubber monomer units.

Polyacrylic acids which are slightly crosslinked such as the CARBOPOLS, commercially available from B. F. Goodrich, are also useful as network polymers in the products of this invention. Polyacrylic acids of this type and other polymers such as polyethylene oxide, cellulosics and polysaccharides act as network polymers and may also contribute to maintaining moisture in the wound. The Aquasorb-D series from Hercules Corporation, which is modified guar gums are examples of modified polysaccharides which are useful in the compositions of this invention by maintaining gel strength. Preferably, one CARBOPOLS polyacrylic acid that would be useful in the compositions of this invention is 934P. It contains the following monomers: acrylic acid monomers with alkyl sucrose as the crosslinker.

The second class of polymers or additives useful in the compositions of this invention are the "flow control polymers", which are chosen to assist in controlling flowability in processing the structured ointment at or about room temperature and film-forming capacity. This lends a more film-like structure to the dressings of this invention as opposed to a gel-like structure. Film-like characteristics are important so as to lend greater integrity at usage temperatures. However, the flowability should not be so great as to permit the compositions to migrate from their desired positions in use on a wound.

The second class of agents, polymers or additives useful in the compositions of this invention also assist in achieving an "ointment feel" to the dressings of this invention. This "ointment feel" can be quantified as the value of the shear elastic compliances and loss compliances of the compositions measured at skin temperatures, (approximately 35° C.) at a testing frequency of 10 radians/second as measured on a Rheometrics RDS 7700 rheometer.

Petrolatum, for example, has a very high shear compliance, greater than $5 \times 10^{-5}$ $cm^2/dyne$ and has a loss compliance greater than $1 \times 10^{-5}$ $cm^2/dyne$. Though petrolatum has an "ointment feel", it is also extremely fluid and therefore unacceptable for use by itself in the dressings of this invention. The balance of "controlled flow" and "ointment feel" falls within the following desirable band of shear compliances: the elastic compliance ranges from about 2 to about $20 \times 10^{-6}$ $cm^2/dyne$ and the loss compliance ranges from 3 to $20 \times 10^{-6}$ $cm^2/dyne$. Above this range, the formulation may have an ointment feel, but its flowability is very high. The desired balance of controlled flow and ointment feel is present within this range. Below this range, the flow is well-controlled, but the composition has a considerably reduced ointment feel.

Preferably, the flow control polymers assist in assuring that, at low temperatures, the viscosity dependence of the compositions of this invention is linear on a log-log plot. This indicates that the compositions of this invention have a controlled, predictable attribute at low, usage temperatures.

Those polymers that assist in controlling flow at low temperatures may be selected from polymers such as polyolefins. Preferably, they are homopolymers, copolymers or polymers composed of several monomers and are not crosslinked. More preferably, this second class of polymers or additives includes the following: ethylene vinyl acetate, or polyalkylenes such as polyisobutylene, ethylene propylene copolymers, polyethylenes and the like. Flow control additives may also preferably be a stearate or palmitate ester, such as a alcohol ester of a fatty acid. Preferably, such an additive may be stearyl alcohol. This class of polymers or additives may also be used to impart some "stickiness" to the composition or may even detackify the composition, depending upon the polymers chosen and their concentrations. For example, polyethylenes added at a concentration of at least 5% may aid in detackifying a composition whereas ethylene vinyl acetate added at a concentration of at least 5% may increase the tackiness of the composition.

Additives may be introduced into the compositions of this invention to influence the "feel" of the final product. The composition should mimic the sensation of ointment products as fully as possible, in order to ensure that the consumer who is accustomed to prior ointment products is comfortable wearing the composition. For example, silicone waxes, common emollients known to those of skill in the art (i.e., polyethylene glycol esters), most preferably, emollients having a stearate or palmitate functional end-groups or the like may be used for this purpose in the dressings of this invention. Dow Corning 580 wax available from Dow Corning, a stearoxy trimethyl silane polymer enhances the ointment feel of the composition by reducing the drag created by the addition of the network and flow control polymers.

Other compounds may be added to the compositions of this invention to increase its hydrophilicity and, still assist in wound healing by maintaining a moist wound environment. For example, castor oil, wool wax alcohol, glycerin, polyethylene glycols, block copolymers of polypropylene oxide and polyethylene oxide and propylene glycol. These compositions absorb a certain amount of water and/or wound fluids, although the rate of absorption is relatively slow. The slow rate of absorption allows the composition to be considered occlusive and, therefore, beneficial to wound healing.

Other compounds may also be added to the compositions of this invention to lend medicinal properties to the product or otherwise cause modification. For example, antiseptics, antibiotics, anesthetics or other medicaments may be added to the composition to assist in wound healing. Examples of such compounds are: neomycin sulfate, polymixin-B sulfate, zinc bacitracin, benzalkonium chloride, cetylpyridium chloride, lidocaine, benzocaine, silver sulfur diazine, hydrocortisone and the combinations thereof and the like. Likewise, skin care agents and therapeutics may be added to the compositions of this invention, for example, retinoid compounds such as tretinoin, retinol, retinaldehyde or the like, alpha hydroxy acids or other products that are well-known. Preferably, the hydrophobic solvent base should be present in the dressings of this invention in an amount from about 50 to about 95% by weight of the composition; more preferably, they should be present in an amount from about 65 to about 85% of the composition; most preferably, they should be present in an amount from about 75 to about 85% of the composition.

The network polymers should be present in the dressings of this invention in an amount from about 0.5 to about 10% by weight of the composition; more preferably, they should be present in an amount from about 2 to about 8% of the composition; most preferably, they should be present in an amount from about 5 to about 7% of the composition.

The flow control agents should be present in the dressings of this invention in an amount from about 0.5 to about 40% by weight of the composition; more preferably, they should be present in an amount from about 3 to about 20% of the composition; most preferably, they should be present in an amount from about 5 to about 10% of the composition.

The predominantly hydrophobic base, in concert with the structured polymer network reduces the dissolution of the active medicaments in the matrix, thereby slowing their leaving the matrix solution. The predominance of an oil-phase in the structure does not allow the wound fluids to readily leach the active ingredients from the structure. The hydrophobicity prevents the material from being completely bioactive, but rather permits it at a controlled rate. For example, neomycin in a completely hydrophilic environment is 100% bioactive and totally available to the wound. This can be extremely irritating to the wound and skin. Furthermore, the hydrophobic structure does not readily break down when in contact with the wound bed. A hydrophilic structure would be more soluble in the hydrophilic wound fluid.

The dressings of the invention can be applied directly to a wound, or may be coated directly onto a film or fiber substrate which is, in turn, applied to the wound and surrounding skin. Such films may be composed of one or more of the following polymers: polyethylene, polypropylene, polyesters, polyvinylacetate. Films useful in the products of this invention may be continuous or discontinuous, i.e., reticulated or having some other regular pattern of "holes".

The dressings of this invention may also be coated onto a fiber substrate which, in turn, is adhesively or otherwise attached to a film substrate. Examples of fiber substrates are fabrics that are knitted such as modified entangled fiber composed of rayon polyesters, or those that are woven, such as flexible fabrics composed of rayon-nylon blends. Non-woven fiber substrates may also be used, such as 90:10 polypropylene-rayon blends, or the like. These dressings can be coated onto a film or fiber material and then further applied to a secondary substrate which holds the dressing in place over the wound. Types of secondary substrates are films or woven or nonwoven fabrics with pressure sensitive adhesives.

The products of this invention are preferably made by blending the constituents in conventional batch mixers such as Brabender Plasticorders, Hobart mixers, Groen mixers, Baker Perkins and the like. Other batch mixers may be used that are capable of applying high shear at elevated temperatures and completely "sweeping" the surface of the bowl or container such that there are no "dead" spots. Continuous mixers may also be used such as Werner Pfleiderer ZSK-30 or American Leistritz ZSE-50. Preferably, the hydrophobic solvent base and optional additives are heated to a suitable temperature, from about 80° C. to about 150° C., prior to addition of the network polymer and flow control polymers. The network and flow control polymers are then blended with the hydrophobic solvent base until they are completely dissolved, i.e. the system is homogeneous and free of gelations. The blend is then preferably coated onto a substrate and cooled to room temperature, resulting in an occlusive structured dressing.

The following examples are merely illustrative of the products of this invention, methods of making such products and methods of using the products. The examples are not intended to limit the scope of the invention.

EXAMPLE 1

To a Brabender Plasticorder heated to 125° C. was added 180 grams of U.S. White petrolatum, 90 grams of Elvax 40W, a poly-vinylacetate from Dupont, 15 grams of mineral oil and 15 grams of Kraton G 1702, a diblock copolymer from the Shell Company composed of polystyrene and ethylenepropylene copolymer. This composition was mixed for 60 minutes and then the temperature was dropped to 80° C. and mixing was continued for another 30 minutes. The formulation was coated onto a nonwoven substrate while still warm (at 80° C.) using a draw down method. Squares approximately ¾ inch in length were centered onto a ¾ inch by 3 inch adhesive strip. A release film with a low release surface was placed onto the strip covering the adhesive and ointment surface. The strips were subjected to a standard ethylene oxide sterilization cycle (30 minutes at 175° F.) in the presence of water. No oozing or flowing out of the ointment from the adhesive strip was observed. No ointment was seen on the adhesive strip.

Referring to FIG. 1, the ethylene oxide sterilization temperature is indicated as a vertical dashed line intersecting the "gelling plateau" region of the viscosity plot, thus indicating that the composition is stable at that temperature and unlikely to flow. In comparison, there is also a dashed line indicating the viscosity-temperature relationship for petrolatum. As indicated by the dashed line, petrolatum would flow readily at about 48° C., far lower that the sterilization temperature. In fact, petrolatum melts at 55° C. and, therefore, would be unacceptable in the products of this invention.

EXAMPLE 2

Using the method of example 1, 210 grams of White Petrolatum, 60 grams of Elvax 40W, 15 grams of Kraton G1702 and 15 grams of Lanolin Alcohol were coated onto a nonwoven substrate. No oozing or flowing of the ointment was also observed. The composition was tested for hydrophilic properties by the observation of the slow absorption of water droplets placed on the coating of this example.

EXAMPLES 3–6 AND COMPARATIVE EXAMPLE A

The following five compositions were made according to the method of example 1 and also coated onto a nonwoven substrate.

| Compound | 3 | 4 | 5 | 6 | A |
|---|---|---|---|---|---|
| Kraton G 1702 | 11.1 | 7.7 | 11.5 | 11.1 | — |
| Petrolatum | 74.1 | 76.9 | 77.0 | 74.1 | 83.3 |
| Elvax 40W | 14.8 | 15.4 | 11.5 | 11.1 | 12.5 |
| Elvax 150W | — | — | — | 3.7 | 4.2 |

Figure 2:
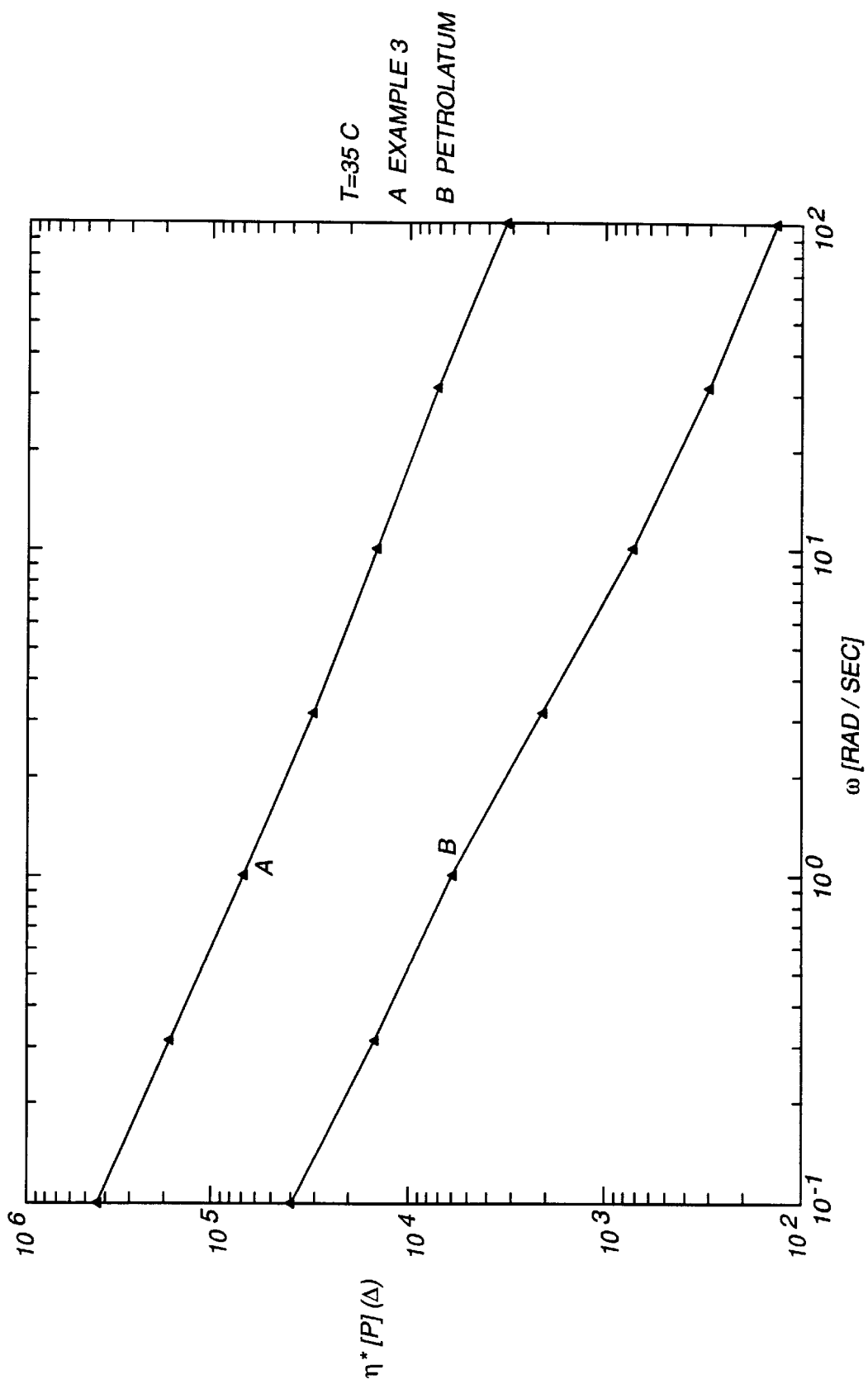
FIG. 2 is a plot showing viscosity as a function of shear rate for petrolatum and for another of the occlusive compositions of the present invention.

The viscosity of the composition of Example 3 as a function of shear rate was measured on a Rheometrics RDS 7700 rheometer at 35° C. and compared to the viscosity of white petrolatum as a function of shear rate. A graph of the results of this measurement is set forth in FIG. 2. An increase in viscosity of a factor of 10 between the White petrolatum and the composition of Example 3 was noted.

Figure 3:
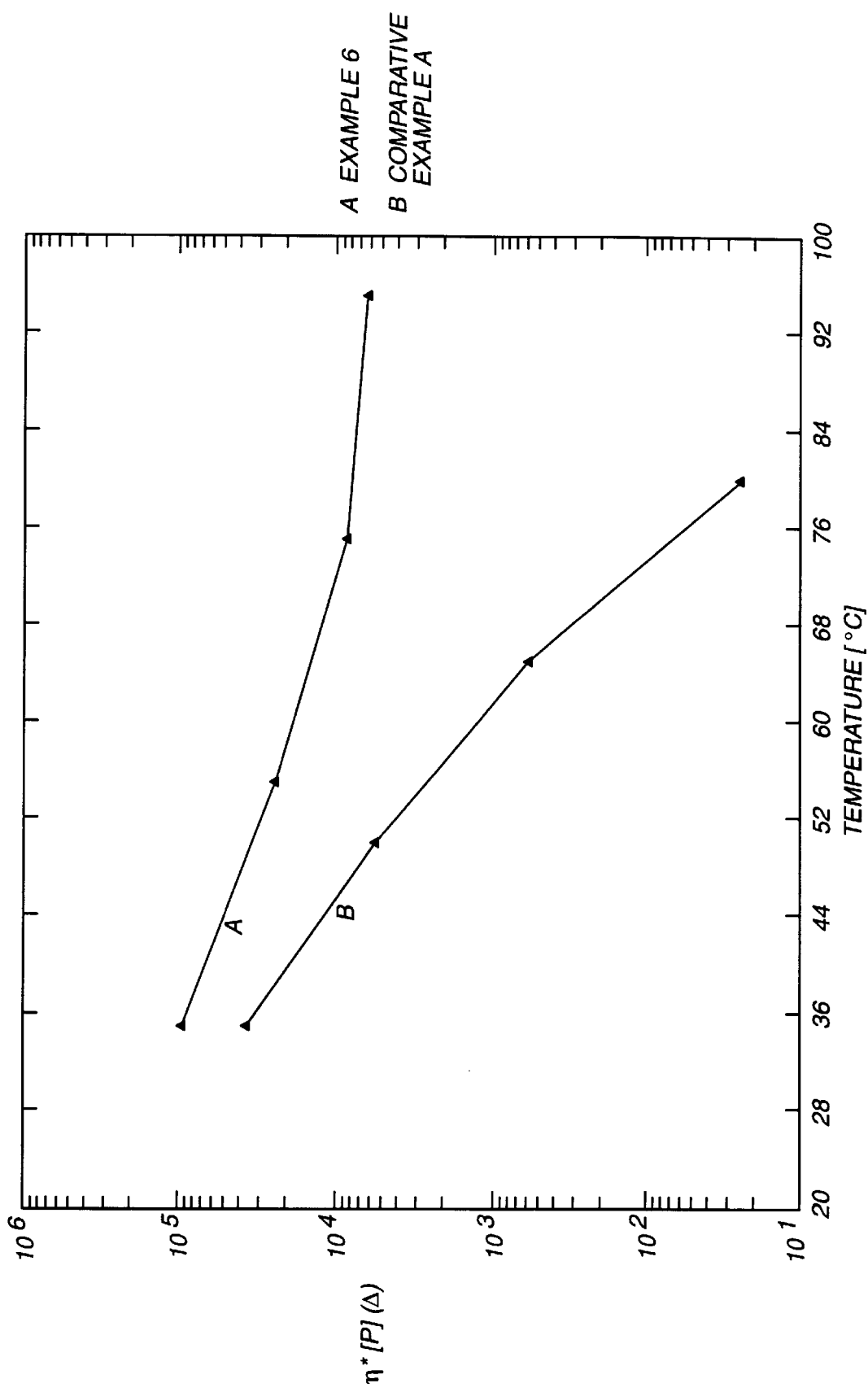
FIG. 3 is a semi-log plot showing viscosity as a function of temperature for yet another occlusive composition of the present invention and a composition (Comparative Example A) prepared for purposes of comparison.

The temperature dependence of the viscosity of compositions of Example 6 and Comparative Example A were compared, the latter containing no "network" polymer. The results of this measurement are set forth as a semi-log graph in FIG. 3. As FIG. 3 illustrates, the viscosity-temperature response of Example A is that which would be expected from essentially linear, noncrosslinked polymers in the melt or in solution: on a log-log plot, the relationship between viscosity and temperature over a limited temperature range is linear. However, the relationship for Example 6 is different. As set forth in FIG. 3, at elevated temperatures, the viscosity plateaus. This is what would be expected from a slightly crosslinked or network polymer or a di-or tri-block copolymer. This plateau is called the gelling region; a fairly stable gel or network is apparent at these temperatures. The network is destroyed only at extremely high temperatures. Example 7 and Comparative Example B

| | 7 | B |
|---|---|---|
| Kraton G1702 | 10.0 | 10.7 |
| USP White Petrolatum | 83.3 | 89.3 |
| Elvax 40W | 6.7 | — |

Figure 4:
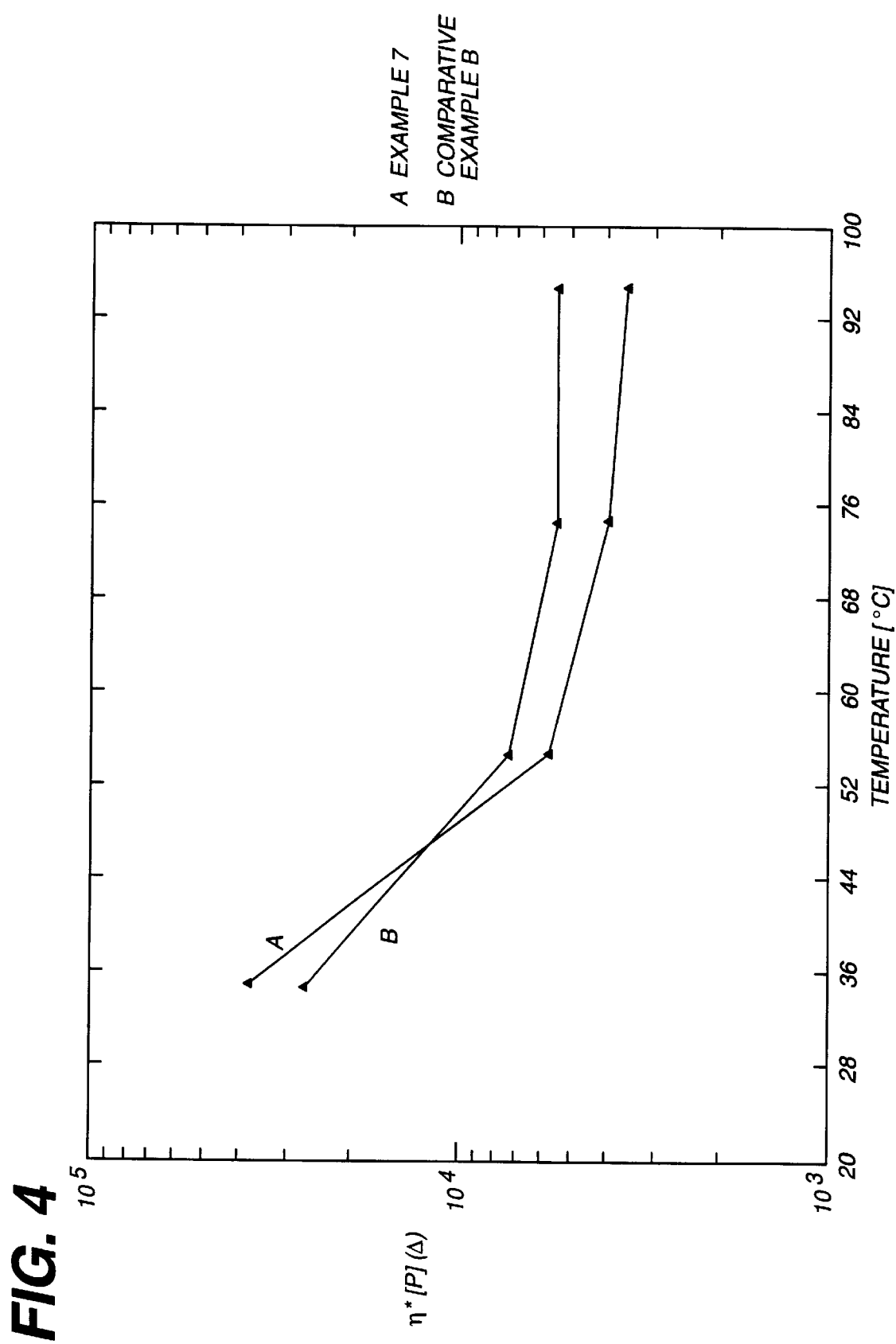
FIG. 4 is a semi-log plot similar to that shown in FIG. 3.

Example 7 was made in accordance with the process described in Example 1 and contains a network polymer, Kraton G1702, petrolatum and a linear polymer, Elvax 40W, which is a polyvinylacetate. Example B does not include a linear polymer. Comparisons were made between Example 7 and Comparative Example B using the same method as set forth in Examples 6 to 9. In FIG. 4 at low temperatures, Example 7, which has a total polymer content of 16.7%, has a higher viscosity than Comparative Example B with a total polymer content of 10.7%. As the temperature increase, the viscosity curves "crossover"; i.e., both sets of data exhibit the gelling plateau, but comparative Example B has a higher plateau viscosity than Example 7. This data indicates that the gelling or network polymer has an important influence at elevated temperatures and the linear polymers find its significance at lower temperatures.

EXAMPLE 8–12

Hydrophilic compositions of this invention were made in accordance with the procedure set forth in Example 1. The following compositions were made:

| Compound | 8 | 9 | 10 | 11 | 12 |
|---|---|---|---|---|---|
| Wool Wax Alcohol | 17 g | 12 g | — | — | — |
| Petrolatum | 40 g | 51 g | 69.2 g | 61.5 g | 72.7 g |
| Mineral Oil | 21 g | 10 g | — | — | — |
| Kraton G1702 | 12 g | 12 g | 7.7 g | 7.7 g | 9.1 g |
| Elvax 40W | 10 g | 5 g | — | 7.7 g | 9.1 g |
| Glycerine | — | 10 g | 15.4 g | 15.4 g | — |
| Pluronic | — | — | .7 g | 7.7 g | 9.3 g |

These compositions exhibited hydrophilic characteristics while maintaining an ointment feel and structured properties. The hydrophilic characteristics were demonstrated by placing a drop of distilled water and timing how long it took for the hydrophilic compositions to absorb water. Typically it took 3–4 minutes. In a comparable test using 100% petrolatum, there was no any perceivable absorption after 30 minutes.

EXAMPLES 13–18

The following compositions were made utilizing the method of Example 1. The figures represent the weight percent of the ingredients set forth below in each composition:

|  | 13 | 14 | 15 | 16 | 17 | 18 |
|---|---|---|---|---|---|---|
| Kraton G1650 | 2 | 2 | — | — | 4 | 3 |
| Kraton G1702 | 10 | 7 | 10 | 10 | 5 | 6 |
| USP petrolatum | 88 | 81 | 60 | 70 | 81 | 81 |
| Steroxytrimethyl-silane | — | 10 | 10 | 10 | 10 | 10 |
| Lanolin Alcohol | — | — | 20 | — | — | — |
| Stearyl alcohol | — | — | — | 10 | — | — |

All the above examples provide non-flowing ointment characteristics at elevated temperatures. Esthetics and release from a silicone coated facing paper or adhesion to skin were modified by adjusting ratios of the Kraton diblock and triblock copolymers. Alternatively, additives such as steroxytrimethylsilane or stearyl alcohol enhance release characteristics from the release paper at ambient temperature and reduce greasiness or tackiness of the ointment on skin. All the above formulations are water insoluble with the exception of Example 15, which includes lanolin alcohol that imparts a water absorption characteristic to the base.

EXAMPLE 19

The composition of Example 14 was used as a base for the following triple antibiotic-containing dressing in accordance with this invention.

|  | Example 19<br>% W/W |
|---|---|
| Kraton G 1650 | 2 |
| Kraton G 1702 | 7 |
| Petrolatum, USP | 79.5 |
| Steroxytrimethylsilane | 10 |
| Bacitracin Zinc | 0.80 |
| Polymyxin B Sulfate | 0.13 |
| Neomycin Sulfate | 0.57 |

A concentrate of the active ingredients was made by adding the antibiotic powders into petrolatum at 60° C.; 2.40 Kg of Bacitracin Zinc, 0.39 Kg of Polymyxin B Sulfate and 1.71 Kg of Neomycin Sulfate was dispersed in 50 Kg of US White Petrolatum using a Ross homogenizer set at 60° C. This concentrate was cooled to room temperature. Separately, 6 Kg of Kraton G1650, 21 Kg of Kraton G1702 and 30 Kg of Steroxytrimethylsilane were compounded in 188.5 Kg of USP White Petrolatum in a sweep kettle at 120° C. until complete solution was obtained. This was cooled down to 80° C. and the antibiotic concentrate was added and mixed for 30 minutes and then cooled. The ointment was heated to 60° C. and extruded onto a padstock where it was finished into a complete product. The antibiotic was tested for antimicrobial activity and retained its activity for at least three months.

EXAMPLE 20

Figure 5:
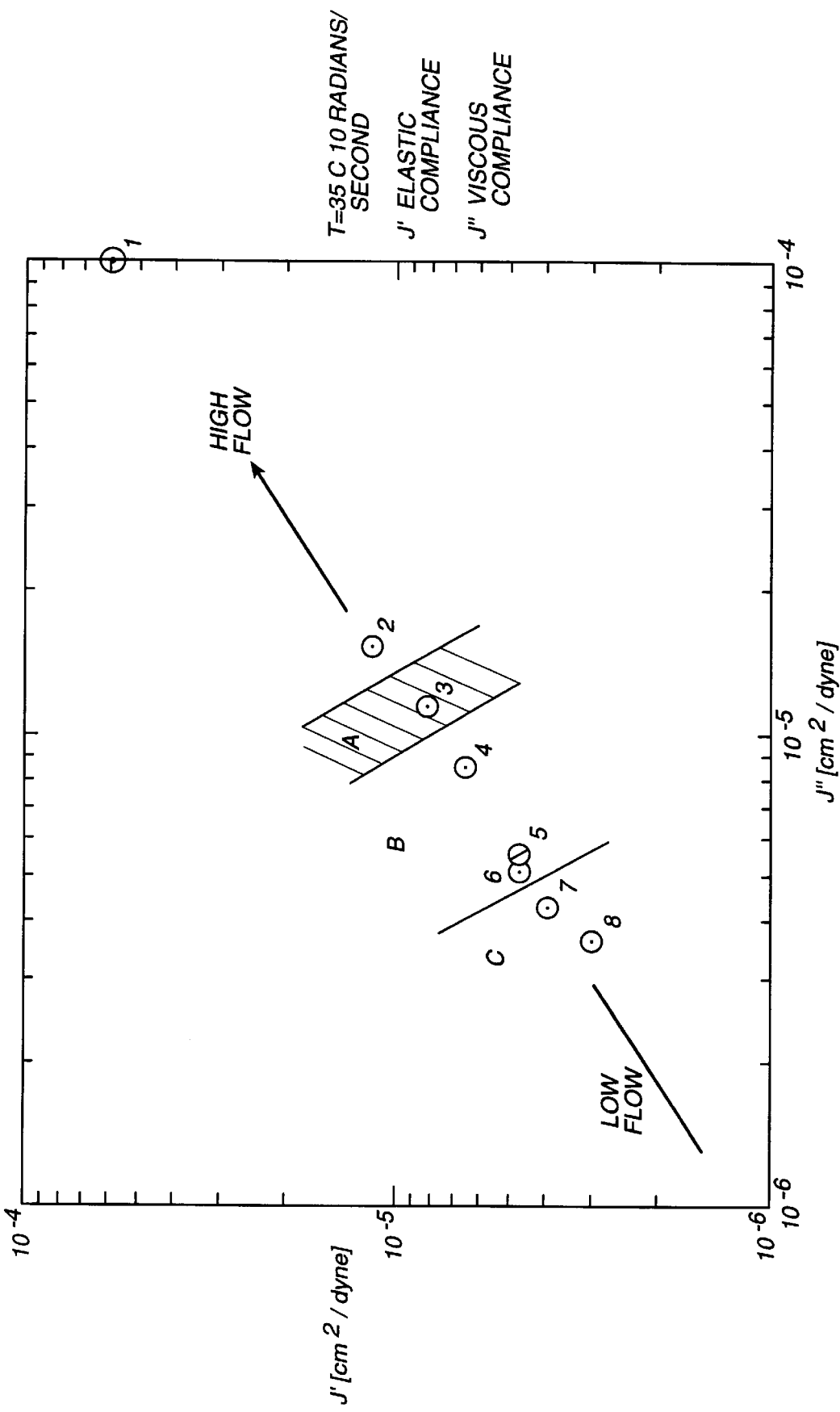
FIG. 5 is a log-log plot showing the shear compliance of petrolatum, six occlusive compositions of the present invention and a composition (Comparative Example B) prepared for purposes of comparison.

The compositions of this invention exhibit a good ointment feel" while maintaining their integrity during use. FIG. 5 depicts a plot of the elastic compliances and loss shear compliances of compositions of this invention at 35° C. J' represents the elastic shear compliance and J" represents the viscous loss shear compliance.

Point 1 represents USP Petrolatum, Point 2 represents Comparative Example B, Point 3 represents Example 7, Point 4 represents Example 14, Point 5 represents Example 18, Point 6 represents Example 6, Point 7 represents Example 17 and Point 8 represents Example 4. The curve indicates the direction of increased flow and soft feel. The area (A), which is shaded, indicates the area of the graph at which products become excessively flowable for use in processing. To the right of the shaded area, the products are too soft for processing. To the left of the shaded area, the products have an ointment feel, but are less flowable and maintain their stability under shear stress. The area marked B represents the preferred balance of controlled flow and "ointment feel"; Example 15 represents such a formula. To the left of B, there is another transition where flow is decreased, which assists the processing of the ointment, but where the desired "ointment feel" is lost. Examples 5 and 6 are at the borderline of acceptability of controlled flow and "ointment feel". In area C the flow is reduced considerably and the "ointment feel" is considerably reduced. Thus, the compositions of this invention exhibit an ointment feel while retaining stability.

EXAMPLE 21

Figure 6:
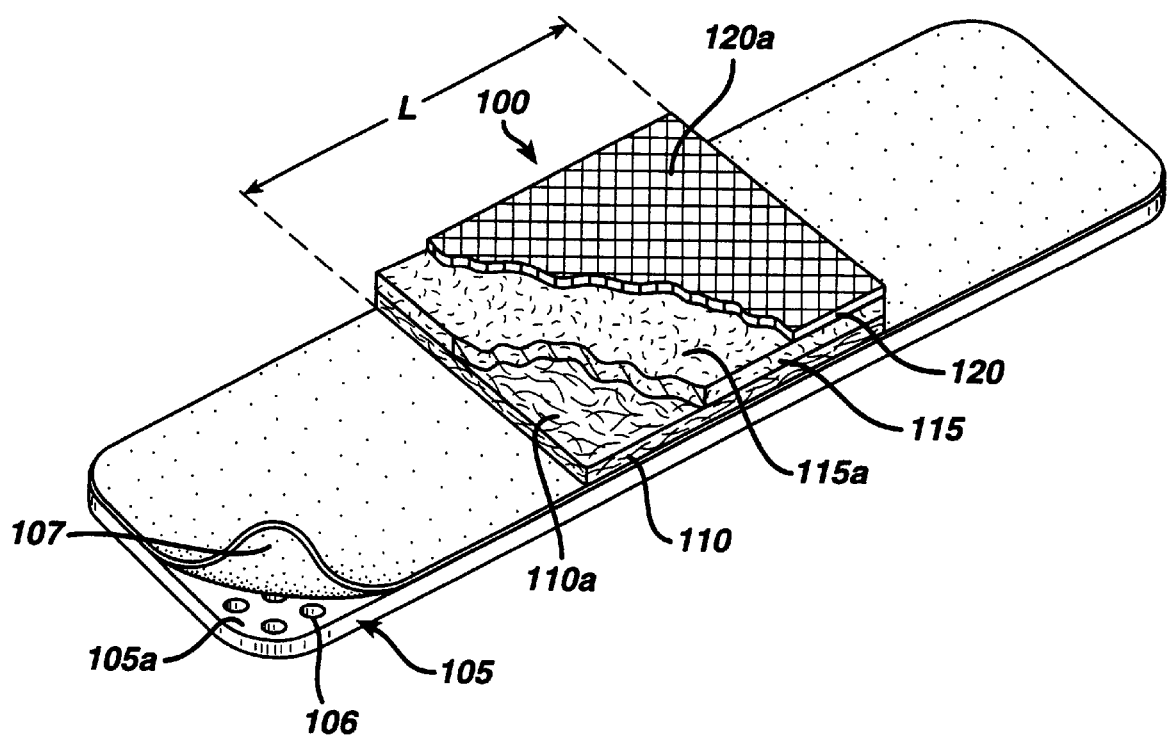
FIG. 6 is a perspective, with portions cut away, of an adhesive bandage comprising one of the occlusive compositions of the present invention.

An adhesive bandage was made using one of the occlusive compositions described earlier herein. This adhesive bandage is illustrated in FIG. 6 of the drawings. As seen in FIG. 6, adhesive bandage 100 comprises a backing material 105 having apertures 106 therein; a support material 110; occlusive composition 115; and a porous covering material 120. The upper surface 105a of the backing material was coated with a layer of a pressure-sensitive acrylic adhesive 107. It will be understood that any of the adhesives well known in the art for use with adhesive bandages may be used in place of this adhesive. The adhesive may, if desired, be deposited on the backing layer in a continuous or discontinuous pattern rather than as an overall coating as illustrated in the drawing.

As is illustrated in the drawings, support material 110 is preferably provided in the form of a fibrous pad which is centered from end-to-end of the backing material and extends from one side of the backing material to the other. It will be understood that support material 110 is secured to the backing material by the aforementioned adhesive 107. The support material 110 used in the bandage of this Example 21 was a nonwoven fabric comprising about 90% by weight of polypropylene fibers and about 10% by weight of rayon fibers. The basis weight of this fabric was 3.7 oz/yd$^2$ and had a thickness of about 34 mils. It will be understood that the support material may comprise nonwoven fabrics other the one described above. In addition, other materials, such as foams, woven fabrics (e.g., gauze), knitted fabrics and the like may be used.

As will also be seen in the drawings, the upper surface 110a of fibrous support material 110 carries and has adhered thereto occlusive composition 115. The occlusive composition is coextensive in length and width with support material 110. As suggested by its name, the function of the support material is to support the occlusive composition which overlies its upper surface. In addition, the support material tends to provide a desirable cushioning effect when the adhesive bandage is applied over a wound site. The upper surface 115a of occlusive composition 115 is covered by a porous covering material 120. In the specific embodiment of this Example 21, porous covering material 120 comprised a porous polyethylene film available from Hercules, Inc., Wilmington, Del., U.S.A. under the designation DELNET™ X-550. Other porous covering materials can be used in place of the aforementioned porous polyethylene films available under the DELNET™ name. For example, the porous covering material can be made of polyvinyl chloride, polypropylene, polyester, nylon or the like polymeric materials instead of polyethylene.

The occlusive composition 115 used in adhesive bandage 100 of this Example 21 was the occlusive composition set forth in foregoing Example 19. The occlusive composition 115 was applied to support material 110 in accordance with the procedure set forth in Example 19 hereinabove. The porous covering material 120 overlies upper surface 115a of occlusive composition 115 and is coextensive in length and width with the occlusive composition and underlying support material 110.

Figure 7:
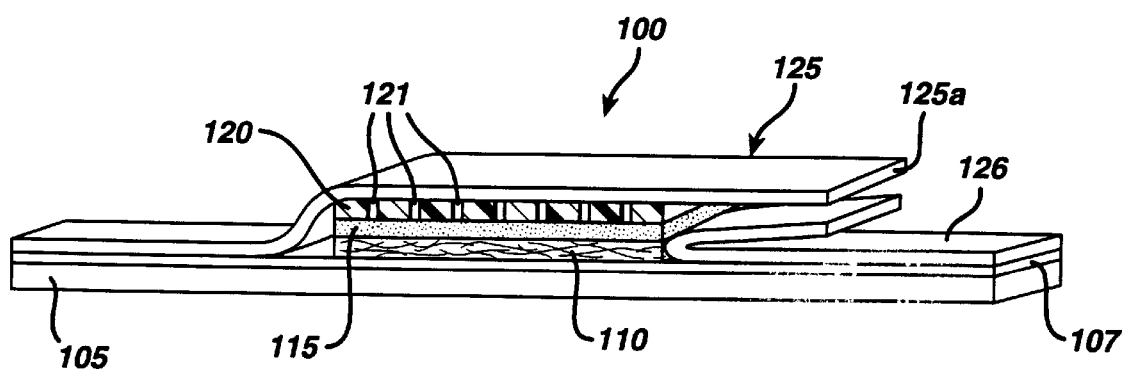
FIG. 7 is a side view, partially in section, of the adhesive bandage illustrated in FIG. 6 wherein the adhesive bandage further comprises release tabs.

Release tabs 125, 126 which comprise silicone-coated polystyrene, were placed over the exposed portions of adhesive 107 and the upper surface of porous covering material 120 in the fashion shown in FIG. 7 of the drawings.

Figure 10:
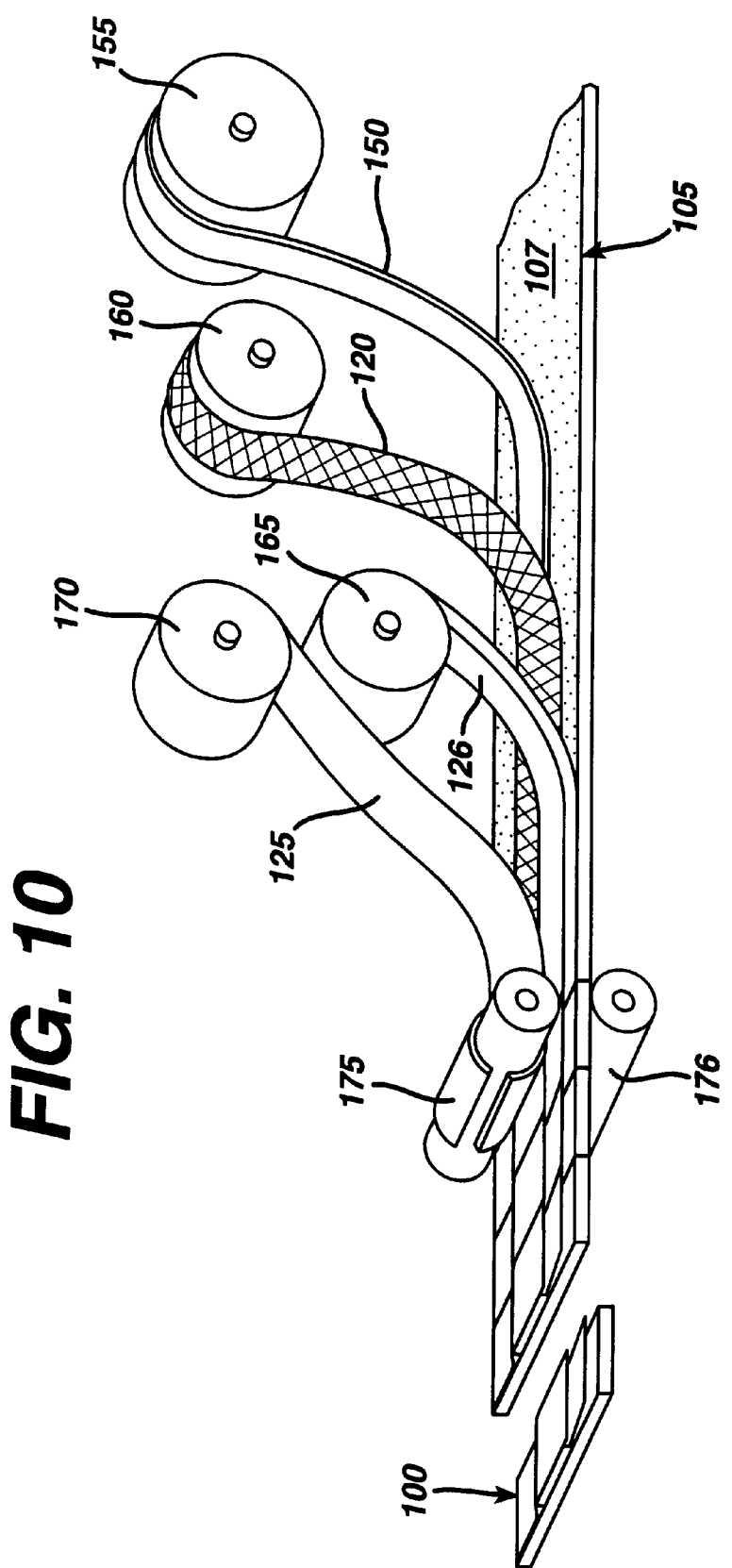
FIG. 10 is a schematic view showing the manufacture of the adhesive bandage shown in FIG. 7.

The adhesive bandage shown in FIG. 7 is made according to a process in which the bandage is oriented at right angles to the direction of travel of the raw materials through the manufacturing apparatus. Briefly, as shown in FIG. 10, the backing material 105 coated with adhesive 107 is conveyed, from right-to-left as viewed in FIG. 10, on top of a conveyor belt (not shown). A web 150 comprising the support material 110 onto which occlusive composition 115 had been previously applied by an extrusion coating process is led off roll 155 and placed on top of the adhesive coated backing material 105. The width of web 150 corresponds to the length, L, of backing material 105 (see FIG. 6).

Porous covering material 120 is led off supply roll 160 and placed on top of web 150. It will be understood that, in the process being described, the width of covering material 120 corresponds substantially to the width of web 150. Release material 126, supplied from roll 165, is folded to the configuration shown in FIG. 7 and applied to the exposed adhesive area at one side of the adhesive coated backing material. Release material 125, supplied from roll 170, is then applied so as to cover the exposed adhesive area at the other side of the adhesive coated backing material as well as the upper surface of porous covering material 120. Release material 125 extends beyond the edge of the porous covering material to provide a grasping tab 125a as illustrated in FIG. 7 of the drawings.

The combined raw materials, assembled as just described, are then passed through the nip of cutter rollers 175, 176. Rollers 175, 176 perform two functions, i.e., they compress the previously assembled raw materials at a pressure of about 10–20 pounds per square inch and, at the same time, cut the traveling, assembled raw materials into individual adhesive bandages 100. The individual adhesive bandages are subsequently wrapped, packaged and sterilized, all according to procedures which are well known in the art.

Figure 7A:
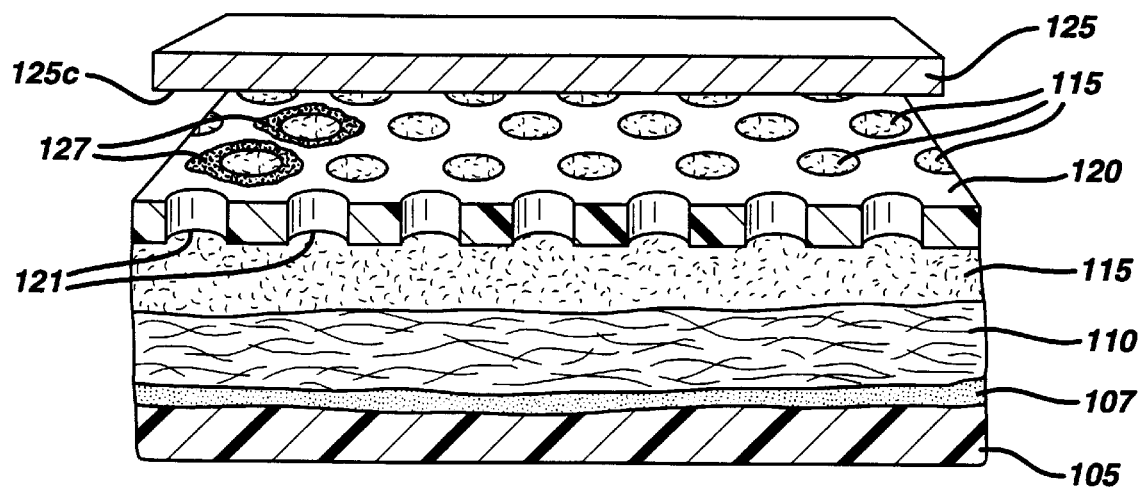
FIG. 7A is a fragmentary view, greatly enlarged and partially in section, of a portion of the adhesive bandage of FIG. 7.

As a result of the just described manufacturing process, particularly as a result of the passage of the raw materials through the nip of rolls 175, 176, the occlusive composition 115 is pressed upwardly into holes 121 in covering material 120 so that said occlusive composition is disposed within said holes and is in intimate contact with the lower surface 125c of release tab 125. This is illustrated in FIG. 7A. Thus, after the release tabs are removed preparatory to use, and the adhesive bandage is applied over a wound site, the wound surface is contacted by the portions of occlusive composition 115 which had previously been in intimate contact with the lower surface 125c of release tab 125. Such contact of the wound surface by the aforementioned portions of occlusive composition 115 is important especially in those instances where said occlusive composition includes a medicament for treatment of the wound.

It will be understood that in some instances, depending on such factors as the manufacturing conditions employed and the rheological characteristics of occlusive composition 115, the occlusive composition 115, after passing upwardly into holes 121, may spread to some extent over the upper surface 120a of porous covering material 120 and beneath the release materials 125. Portions of occlusive composition 115 which have spread over the upper surface of the porous covering material are identified by numeral 127 in FIG. 7A.

EXAMPLE 22

Figure 8:
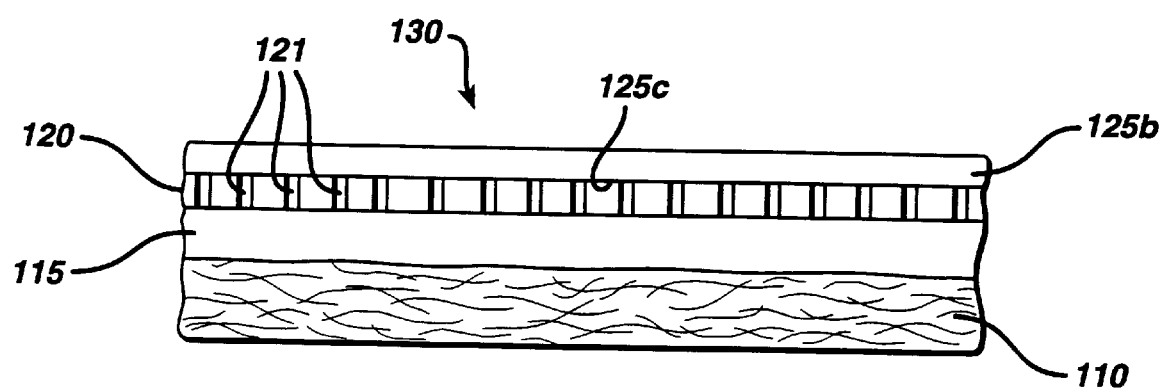
FIG. 8 is a sectional side view of a typical test specimen.

Seven different test specimens, identified by numeral 130 in FIG. 8, were prepared. Test specimens 130 comprised fibrous support material 110, an occlusive composition 115, porous covering material 120, and a portion 125b of a release sheet material. Fibrous support material 110 was the 90:10 (weight percentage) polypropylene rayon fabric described earlier. Occlusive composition 115 was that described in Example 19. Each of the seven test specimens 130 used a different porous covering material 120 as described in Table I. The release sheet material 125b used for these seven test specimens was a clear untreated polyethylene film having a thickness of about 4 mils as described in Table I.

Three controls were also used. Control #1 consisted of fibrous support material 110, occlusive composition 115, and release sheet material 125b. No porous covering material 120 was employed. The release sheet material 125b for Control #1 was a silicone coated polystyrene film having a thickness of about 4 mils.

Control #2 consisted of fibrous support material 110, occlusive composition 115, and release sheet material 125b. No porous covering material 120 was employed. The release sheet material 125b for Control #2 was a clear untreated polyethylene film having a thickness of 4 mils.

Control #3 consisted of fibrous support material 110, occlusive composition 115, a nonporous covering material 120 consisting of polyethylene, and release sheet material 125b. In Control #3, both the nonporous covering material 120 and the release sheet material 125b were a clear untreated polyethylene film having a thickness of 4 mils.

The material used for the porous covering material 120 comprised a porous polyethylene film known as DELNET™ available from Hercules, Inc. Various porous polyethylene films available under the DELNET™ trademark were used to prepare test specimens 22.3 and 22.5–22.10 inclusive. these are listed in TABLE I, second column from the left. These materials had various % open areas (TABLE I, third column from the left) and various hole shapes (TABLE I, fifth column from the left). In addition, TABLE I, fourth column from the left, shows maximum included circle diameters for the various DELNET™ materials. The term "maximum included circle diameter" refers to the diameter of the largest circle which can be inscribed in the opening of each porous covering material.

The individual test specimens listed in TABLE I were tested under conditions similar to those encountered during manufacture and use of the bandage. Each test specimen was rolled twice (i.e., once forward and once backward) with a ten pound roller to press the release sheet 125b into contact with the porous covering material 120 to simulate the pressure to which a bandage product would be exposed during manufacture. The test specimens were then conditioned by placing them under a 0.25 lb load, in an oven at 37° C. for eight hours.

The conditioned specimens were then tested as follows. Each of test specimens 22.3 and 22.5–22.10 inclusive was tested by removing its release sheet material 125b from the top surface 120a of its porous covering material 120. Control #1 (Example 22.1) and Control #2 (Example 22.2) were tested by removing their respective release sheet materials 125b from the upper surface of their respective occlusive compositions 115a. Control #3 (Example 22.4) was tested by removing its release sheet material 125b from its underlying nonporous covering material 120. The force necessary for removal was measured for the seven test specimens containing the DELNET™ porous covering materials and for control specimens #2 and #3. All specimens were observed to determine whether the occlusive composition 115 had delaminated from its underlying fibrous support material 110 during removal of the release sheet material 125b. The occlusive composition 115 was considered to have delaminated from its underlying support material 110 if the underlying support material was visible to the eye as viewed from a direction perpendicular to the top surface 115a of the underlying support material.

EXAMPLE 22.2

The second specimen tested was Control Specimen #2. The specimen has no porous covering as described in Table I.

The release sheet material 125b was a clear untreated polyethylene film as described in Table I. The force necessary for removal of the release sheet material 125b from the occlusive composition 115 was 2.31 grams. It was observed that the occlusive composition 115 delaminated from its underlying fibrous support 110.

EXAMPLE 22.3

The third specimen tested contained a porous cover material 120 with a percent open area of 88% as described in Table I. The porous covering material 120 was identified as DELNET RB0404-28P as described in Table I. The release sheet material 125b was a clear untreated polyethylene film as described in Table I. The force necessary for removal of the release sheet material 125b from the porous covering material 120 was 2.22 grams. The occlusive com-

TABLE I

| Example | Porous covering material (120) | % Open area | Max included circle diameter | Shape of hole | Release sheet material (125b) | Release force grams | Delamination occurs |
|---------|-------------------------------|-------------|------------------------------|---------------|-------------------------------|---------------------|---------------------|
| 22.1 | None (Control #1) | 100% | None | None | Silicone-Coated Polystyrene | Not measured | Yes |
| 22.2 | None (Control #2) | 100% | None | None | Polyethylene | 2.31 | Yes |
| 22.3 | DELNET RB0404-28 | 88% | 1350 microns | Rectangle | Polyethylene | 2.22 | No |
| 22.4 | Nonporous (Control #3) | Zero | None | None | Polyethylene | 0.00 | No |
| 22.5 | DELNET P520 | 15% | 260 microns | Triangle | Polyethylene | 0.00 | No |
| 22.6 | DELNET CKX215 | 28% | 1040 microns | Oval | Polyethylene | 0.27 | No |
| 22.7 | DELNET D220 | 31% | 310 microns | Oval | Polyethylene | 0.32 | No |
| 22.8 | DELNET X530 | 42% | 371 microns | Triangle | Polyethylene | 0.55 | No |
| 22.9 | DELNET X550 | 55% | 441 microns | Triangle | Polyethylene | 0.88 | No |
| 22.10 | DELNET KX215 | 62% | 1380 microns | Triangle | Polyethylene | 1.23 | No |

EXAMPLE 22.1

The first specimen tested was Control Specimen #1. The specimen contained no porous cover material 120 as described in Table I. The release sheet material 125b was silicone-coated polystyrene as described in Table I. Silicone-coated polystyrene is the release material which is preferred for an actual bandage product. It was observed that the occlusive composition 115 delaminated from its underlying fibrous support 110 a portion of the time.

In view of the delamination observed in Control Specimen #1, it became necessary to determine if a porous covering material 120 could be used to prevent such delamination. Furthermore, should a porous covering material 120 prevent delamination, it is then necessary to determine the maximum percent open area for the porous covering material 120 at which delamination does not occur. To ensure that the determined maximum percent open area would prevent delamination, clear untreated polyethylene was used as the release sheet material 125b for the remaining specimens as described in Table I. Polyethylene creates a greater release force than the silicone-coated polystyrene, and hence amplifies the occurrence of delamination. Therefore, should delamination of the occlusive composition 115 from its underlying fibrous support 110 not occur with the removal of the polyethylene release sheet 125b, it is virtually certain it will not occur with the removal of the silicone-coated polystyrene release sheet material 125b which is preferred for an actual product.

position 115 did not delaminate from its underlying support 110. This example shows that the critical upper limit for the percent open area of the porous covering material 120 to prevent delamination is 88% or greater.

EXAMPLES 22.4–22.10

The fourth specimen tested (Example 22.4) was Control Specimen #3. The specimen had a nonporous covering material 120 was polyethylene. The release sheet material 125b was a clear untreated polyethylene film. The force necessary for removal of the release sheet material 125b from the nonporous covering material 120 was zero grams. The occlusive composition 115 did not delaminate from its underlying support 110.

The fifth specimen tested (Example 22.5) contained a porous cover material 120 with a percent open area of 15% as described in Table I. The porous covering material 120 was identified as DELNET P520. The release sheet material 125b was a clear untreated polyethylene film. The force necessary for removal of the release sheet material 125b from the porous covering material 120 was 0.0 grams. The occlusive composition 115 did not delaminate from its underlying support 110.

The sixth specimen tested (Example 22.6) contained a porous cover material 120 with a percent open area of 28% as described in Table I. The porous covering material 120 was identified as DELNET CKX215. The release sheet material 125b was a clear untreated polyethylene film. The force necessary for removal of the release sheet material 125b from the porous covering material 120 was 0.27 grams. The occlusive composition 115 did not delaminate from its underlying support 110.

The seventh specimen tested (Example 22.7) contained a porous cover material 120 with a percent open area of 31% as described in Table I. The porous covering material 120 was identified as DELNET D220. The release sheet material 125b was a clear untreated polyethylene film. The force necessary for removal of the release sheet material 125b from the porous covering material 120 was 0.32 grams. The occlusive composition 115 did not delaminate from its underlying support 110.

The eighth specimen tested (Example 22.8) contained a porous cover material 120 with a percent open area of 42% as described in Table I. The porous covering material 120 was identified as DELNET X530. The release sheet material 125b was a clear untreated polyethylene film. The force necessary for removal of the release sheet material 125b from the porous covering material 120 was 0.55 grams. The occlusive composition 115 did not delaminate from its underlying support 110.

The ninth specimen tested (Example 22.9) contained a porous cover material 120 with a percent open area of 55% as described in Table I. The porous covering material 120 was identified as DELNET X550. The release sheet material 125b was a clear untreated polyethylene film. The force necessary for removal of the release sheet material 125b from the porous covering material 120 was 0.88 grams. The occlusive composition 115 did not delaminate from its underlying support 110.

The tenth specimen tested (Example 22.10) contained a porous cover material 120 with a percent open area of 62% as described in Table I. The porous covering material 120 was identified as DELNET KX215. The release sheet material 125b was a clear untreated polyethylene film. The force necessary for removal of the release sheet material 125b from the porous covering material 120 was 1.23 grams. The occlusive composition 115 did not delaminate from its underlying support 110.

Figure 9:
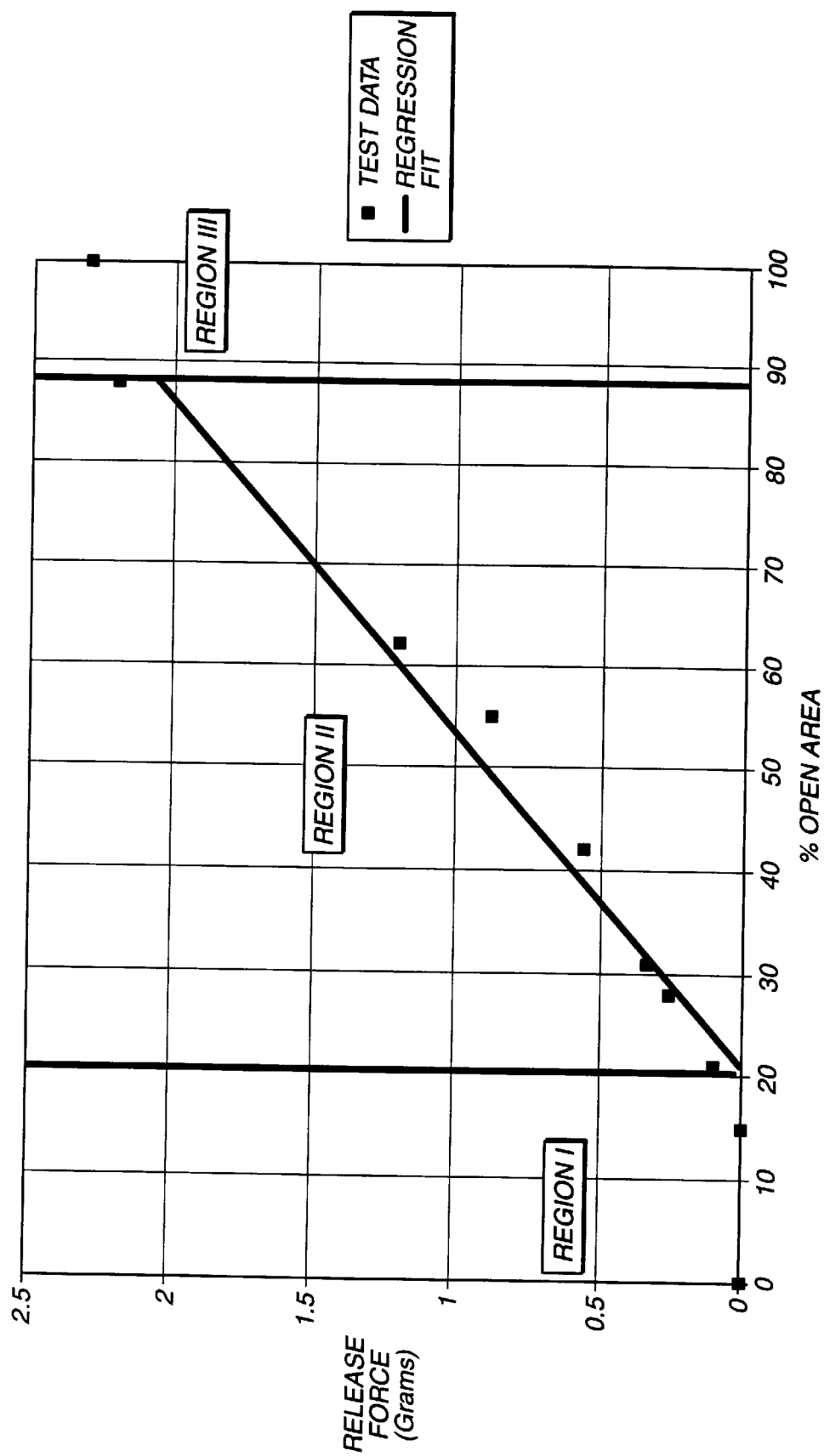
FIG. 9 is a graph of the release force required to remove a release tab from a porous covering material as a function of the percent open area of the porous covering material.

FIG. 9 graphically displays the force necessary for removal of the release sheet material 125b from the porous covering material 120a (hereinafter called release force) versus the percent open area for examples 22.2 through 22.10.

Certain regions appear in FIG. 9, each region characterized by a different slope. Region I contains Examples 22.4 and 22.5, and includes percent open areas of the porous covering material 120, from zero to about 20%.

The release force in this region was measured as zero. The zero release force of Examples within this region reflects a percent open area of the porous covering material 120 which is too small to permit the occlusive composition 115 to penetrate through the holes 121 of the porous covering material 120 and contact the lower side of the release sheet material 125c. As described in Example 21, it is important that the occlusive composition 115 penetrate through the holes 121 of the porous covering material 120 for an effective bandage application. Therefore, the percent open areas of Examples within this region are not suitable for the occlusive composition 115 of the preferred viscosity range.

Region II contains Examples 22.6, 22.7, 22.8, 22.9, 22.10 and 22.3, and includes percent open areas of the porous covering material 120 of about 20% to about 88%. This region is characterized by all measured release forces exceeding zero, and by a linear increase in release force with percent open area. The release forces exceeding zero indicates that for all Examples within this region the occlusive composition does penetrate through the holes 121 of the porous covering and does contact the lower side of the release sheet material 125c. hence, the percent open areas of the Examples in this region are suitable for an effective bandage application. Although measurements were made for representative opening shapes in the porous covering material 120 and representative opening sizes in the porous covering material 120, the results from these measurements were found to correlate on percent open area alone. To determine the minimum percent open area of the porous covering material 120 required for the occlusive composition 115 to penetrate through the holes 121 of the porous covering material 120 and to contact the lower side of the release sheet material 125c to the covering surface, a linear regression curve was fitted to the data in this region. The regression line intercepts the zero release force axis at about 20 percent open area. These data indicate that the critical minimum open area permitted by the invention for the porous covering material 120 is about 20%.

Although the Examples 21 and 22 have focused on the preferred properties of the occlusive composition, those skilled in the art will recognize that the porous coating material can be used at other viscosities, pressures, and temperatures. Although such conditions have not been actually tested, those skilled in the art will realize that the inventive concepts described within Examples 21 and 22 remain valid.

Figure 11:
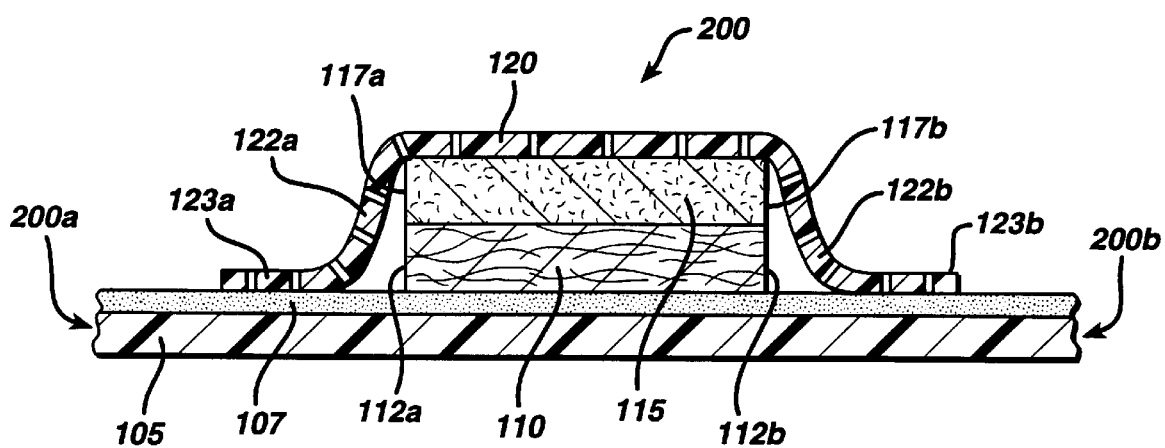
FIG. 11 is a longitudinal section of another embodiment of an adhesive bandage of the present invention in which the porous covering material has been given an alternative configuration.

Referring now to FIG. 11, there is illustrated in longitudinal section an adhesive bandage 200 in which porous covering material 120 has been given an alternative configuration. As was the case with adhesive bandage 100 illustrated in FIG. 6, adhesive bandage 200 comprises backing 105; adhesive layer 107; fibrous support material 110; occlusive composition 115; and porous covering material 120. In bandage 100 disclosed in FIG. 6, porous covering material 120 was coextensive in its length and width with both occlusive composition 115 and with fibrous support material 110. In the alternative embodiment illustrated in FIG. 11, porous covering material 120 comprises downwardly extending portions 122a, 122b and longitudinally extending tab portions 123a, 123b. Downwardly extending portions 122a, 122b serve to cover the ends 112a, 112b, respectively, of fibrous support material 110 and the ends 117a, 117b, respectively, of occlusive composition 115. As will be seen by reference to FIG. 11, ends 112a and 117a face end edge 200a of adhesive bandage 200, while ends 112b and 117b face end edge 200b of the adhesive bandage. Tab portion 123a of porous cover material 120 extends longitudinally for a short distance, e.g., about one-eighth of an inch, toward end edge 200a of bandage 200 while tab portion 123b extends a short distance toward end edge 200b.

The advantage of providing porous cover material 120 with downwardly extending portions 122a, 122b and tab portions 123a, 123b is that longitudinal movement of occlusive composition 115 (i.e., movement toward either or both of ends 200a, 200b of bandage 200) is substantially prevented.

In addition, this configuration of porous covering material 120 helps to insure that support material 110 remains firmly in its centered location between ends 200a, 200b of the bandage.

What is claimed is:

1. An occlusive wound care dressing comprising a backing material, a support material, an occlusive composition and a porous covering material, said backing material having applied thereto an adhesive which secures said support material to said backing material; said occlusive composition overlying the upper surface of said support material; said porous covering material overlying at least the upper surface of said occlusive composition.

2. The wound care dressing of claim 1 wherein the porous covering material has a percent open area of at least about 20%.

3. The wound care dressing of claim 1 wherein the porous covering material has a percent open area not greater than about 88%.

4. The wound care dressing of claim 1 wherein the porous covering material has a percent open area of from about 20% to about 88%.

5. The wound care dressing of claim 1 wherein at least some of said occlusive composition is disposed within the holes of said porous covering material.

6. The wound care dressing of claim 1 wherein said support material is selected from the group consisting of nonwoven fabrics, woven fabrics, knitted fabrics and foams.

7. The wound care dressing of claim 1 wherein said support material is a nonwoven fabric.

8. The wound care dressing of claim 7 wherein said nonwoven fabric comprises a blend of polyester and rayon fibers.

9. The wound care dressing of claim 1 wherein said porous covering material comprises a polymer selected from the group consisting of polyvinyl chloride, polyethylene, polypropylene, polyester and nylon.

10. The wound care dressing of claim 9 wherein the polymeric material comprising said porous covering material is polyethylene.

11. The wound care dressing of claim 1 wherein said porous covering material comprises a pair of downwardly extending portions and a pair of longitudinally extending tab portions.

12. The wound care dressing of claim 1 wherein said occlusive composition comprises
   a) a hydrophobic solvent base compound;
   b) a network polymer; and
   c) a flow control agent.

13. The wound care dressing of claim 12 wherein said composition further comprises at least one agent selected from the group consisting of antiseptics, antibiotics, anesthetics, antiinflammatories, antimicrobials skin care agents and therapeutics, and antipyretics.

14. The wound care dressing of claim 1 wherein the occlusive composition is coextensive in length and width with the support material.

15. The wound care dressing of claim 1 wherein the porous covering material is coextensive in length and width with the occlusive composition.

16. The wound care dressing of claim 1 wherein said porous covering material is a porous film.

17. The wound care dressing of claim 1 wherein the porous covering material has a lower surface facing the occlusive composition and an opposite upper surface, and wherein at least some of the occlusive composition is disposed on the upper surface of the porous covering material.

18. The wound care dressing of claim 1 wherein said occlusive composition is hydrophobic.

19. The wound care dressing of claim 1 wherein said occlusive composition is hydrophilic.

20. The wound care dressing of claim 1 wherein said occlusive composition comprises at least one agent selected from the group consisting of antiseptics, antibiotics, anesthetics, antiinflammatories, antimicrobials, skin care agents and therapeutics, and antipyretics.

21. The wound care dressing of claim 12 wherein said hydrophobic solvent base compound comprises at least one compound selected from petrolatum, mineral oil and an oil derived from fatty acids.

22. The wound care dressing of claim 12 wherein the hydrophobic solvent base compound comprises from about 50 to about 95 percent by weight of the occlusive composition.

23. The wound care dressing of claim 12 wherein the network polymer comprises at least one polymer selected from di-, tri- or multiarm block copolymers of polystyrene and a synthetic rubber, crosslinked poly(acrylic acids), polyethyleneoxide, cellulosics and polysaccharides.

24. The wound care dressing of claim 12 wherein the network polymer comprises from about 0.5 to about 10.0 percent by weight of the occlusive composition.

25. The wound care dressing of claim 12 wherein the flow control agent comprises at least one material selected from poly (ethylene-vinyl acetate), polyalkylenes, esters of fatty acids, silicone waxes, and emollients.

26. The wound care dressing of claim 12 wherein the flow control agent comprises about 0.5 to about 40 percent by weight of the occlusive composition.

27. The wound care dressing of claim 13 wherein the agent comprises at least one compound selected from neomycin sulfate, polymixin-B sulfate, zinc bacitracin, benzalkonium chloride, cetyl pyridinium chloride, lidocane, benzocaine, hydrocortisone, retinoid compounds and alpha hydroxy acids.

28. The wound care dressing of claim 20 wherein the agent comprises at least one compound selected from neomycin sulfate, polymixin-B sulfate, zinc bacitracin, benzalkonium chloride, cetyl pyridinium chloride, lidocane, benzocaine, hydrocortisone, retinoid compounds and alpha hydroxy acids.

29. An occlusive wound care dressing comprising a backing material, a support material, an occlusive composition and a porous covering material, said backing material having applied thereto an adhesive which secures said support material to said backing material; said occlusive composition overlying the upper surface of said support material; said porous covering material overlying at least the upper surface of said occlusive composition; said occlusive composition comprising:
   a) at least one hydrophobic solvent base compound selected from petrolatum, mineral oil and an oil derived from fatty acids;
   b) at least one network polymer selected from di-, tri- or multiarm block copolymers of polystyrene and a synthetic rubber, crosslinked poly(acrylic acids), polyethyleneoxide, cellulosics and polysaccharides; and
   c) at least one flow control agent selected from poly (ethylene-vinyl acetate), polyalkylenes, esters of fatty acids, silicone waxes, and emollients.

30. The dressing of claim 29 wherein the backing material comprises a material selected from films, woven fabrics and nonwoven fabrics.

31. The dressing of claim 29 wherein the backing material is perforated.

32. The dressing of claim 29 wherein the support material comprises a material selected from nonwoven fabrics, woven fabrics, knitted fabrics and foams.

33. The dressing of claim 29 wherein the adhesive comprises an acrylic adhesive.

34. The dressing of claim 29 wherein said porous covering material comprises a porous film.

35. The dressing of claim 29 wherein said porous covering material comprises a polymer selected from polyvinyl chloride, polyethylene, polypropylene, polyester and nylon.

36. The dressing of claim 29 wherein the occlusive composition is coextensive in length and width with said support material.

37. The dressing of claim 29 wherein said porous covering material is coextensive in length and width with said occlusive composition.

38. The dressing of claim 29 wherein said porous covering material comprises a pair of downwardly extending portions and a pair of longitudinally extending tab portions.

39. The dressing of claim 29 wherein at least some of said occlusive composition is disposed within the holes of said porous covering material.

40. The dressing of claim 29 wherein the porous covering material has a lower surface facing the occlusive composition and an opposite upper surface, and wherein at least some of the occlusive composition is disposed on the upper surface of the porous covering material.

41. The wound care dressing of claim 29 wherein said composition further comprises at least one agent selected from antiseptics, antibiotics, anesthetics, antiinflammatories, antimicrobials, skin care agents and therapeutics, and antipyretics.

42. The wound care dressing of claim 29 wherein the hydrophobic solvent base compound comprises from about 50 to about 95 percent by weight of the occlusive composition.

43. The wound care dressing of claim 29 wherein the network polymer comprises from about 0.5 to about 10.0 percent by weight of the occlusive composition.

44. The wound care dressing of claim 29 wherein the flow control agent comprises about 0.5 to about 40 percent by weight of the occlusive composition.

45. The wound care dressing of claim 29 wherein the occlusive composition has a gel strength of about 1,000 to about 10,000 poise over a temperature range of about 50 to about 95° C.

46. The wound care dressing of claim 29 wherein the occlusive composition has an elastic compliance of about $2 \times 10^{-6}$ to about $20 \times 10^{-6}$ cm$^2$/dyne and a loss compliance of about $3 \times 10^{-6}$ to about $20 \times 10^{-6}$ cm$^2$/dyne.

47. The wound care dressing of claim 29 wherein the network polymer comprises a di-, tri- or multiarm block copolymer of polystyrene and synthetic rubber and the synthetic rubber is derived from isoprene, ethylene butadiene or ethylene propylene.

48. The wound care dressing of claim 29 wherein the hydrophobic solvent base compound comprises petrolatum.

49. The wound care dressing of claim 29 wherein the flow control agent comprises a silicone wax.

50. The wound care dressing of claim 41 wherein the agent comprises at least one compound selected from neomycin sulfate, polymixin-B sulfate, zinc bacitracin, benzalkonium chloride, cetyl pyridinium chloride, lidocane, benzocaine, hydrocortisone, retinoid compounds and alpha hydroxy acids.

51. The wound care dressing of claim 47 wherein the network polymer comprises a mixture of a styrene-ethylene/propylene di-block copolymer and a styrene-ethylene/butylene-styrene tri-block copolymer.

52. A process for making an occlusive wound dressing, said dressing comprising a support material and an occlusive composition, said process comprising the steps of
  a) providing a web of support material;
  b) providing an occlusive composition comprising:
    (i) at least one hydrophobic solvent base compound selected from petrolatum, mineral oil and an oil derived from fatty acids;
    (ii) at least one network polymer selected from di-, tri- or multiarm block copolymers of polystyrene and a synthetic rubber, crosslinked poly(acrylic acids), polyethyleneoxide, cellulosics and polysaccharides; and
    (iii) at least one flow control agent selected from poly (ethylene-vinyl acetate), polyalkylenes, esters of fatty acids, silicone waxes, and emollients; and
  c) extruding the occlusive composition onto said support material.

53. The process for making an occlusive wound dressing of claim 52 wherein said dressing further comprises an adhesive-coated backing material, said process further comprising the steps of:
  d) providing a web of an adhesive-coated backing material; and
  e) applying the web produced in step (c) to the adhesive-coated backing material.

54. The process of making an occlusive wound dressing of claim 53, said dressing further comprising a porous covering material, said process further comprising:
  f) providing a web of porous covering material; and
  g) applying the porous covering material to the web produced in step (e).

55. The process of making an occlusive wound dressing of claim 54, said dressing further comprising at least one release tab, said process further comprising the steps of
  h) providing at least one web of release tab material; and
  i) applying said release tab material to the web produced in step (g) so as to contact the exposed adhesive surface of the adhesive-coated backing material with the release tab material.

56. The process of making an occlusive dressing of claim 55 which further comprises the step of
  j) passing the web produced in step (i) into the nip of a pair of compression rollers so as to compress the web of step (i).

57. The process of making an occlusive dressing of claim 56 which further comprises the step of
  k) cutting the web of step (j) into individual adhesive-coated bandages.

58. The process of claim 57 wherein steps (j) and (k) are effected simultaneously.

* * * * *